United States Patent [19]

Champseix et al.

[11] Patent Number: 4,907,463
[45] Date of Patent: Mar. 13, 1990

[54] LINEAR DISPLACEMENT SAMPLING VALVE AND A DEVICE FOR FIXING SAME

[75] Inventors: Henri Champseix, Montesson; Serge Champseix, Les Mureaux, both of France

[73] Assignee: ABX, Sartrouville, France

[21] Appl. No.: 263,810

[22] Filed: Oct. 28, 1988

[30] Foreign Application Priority Data

Oct. 30, 1987 [FR] France .................. 87 15045

[51] Int. Cl.⁴ .................. G01N 1/10; F16K 11/065
[52] U.S. Cl. .................. 73/863.73; 251/325
[58] Field of Search .......... 73/863.73, 863.72, 864.83, 73/864.84, 863.71; 137/625.68, 625.38, 625.39; 251/325

[56] References Cited

U.S. PATENT DOCUMENTS

| | | |
|---|---|---|
| 3,567,339 | 3/1971 | Coulter et al. .......... 137/247.13 X |
| 3,908,463 | 9/1975 | Bedo et al. .......... 251/187 X |
| 3,990,853 | 11/1976 | Godin .......... 73/864.84 X |
| 3,991,055 | 11/1976 | Godin et al. .......... 73/864.84 X |
| 4,493,476 | 1/1985 | Strickland et al. .......... 251/176 |
| 4,691,580 | 9/1987 | Fosslian .......... 73/864.84 |
| 4,726,237 | 2/1988 | Yung .......... 73/864.83 |

Primary Examiner—Tom Noland
Attorney, Agent, or Firm—Fleit, Jacobson, Cohn, Price, Holman & Stern

[57] ABSTRACT

A linear displacement sampling valve and its fixing device are provided, the central assembly of the valve, formed by an element sliding between two fixed guide parts (2) placed on each side, being held in position on four of its faces by lower (7) and upper (8) guides, a metal plate (10) and a base (11) which are fixed members; it is held in position at its end by a manual release locking flange (14) and on one side by a rocker (18) returned by a spring (26) against the lateral face of a fixed guide part (2).

12 Claims, 2 Drawing Sheets

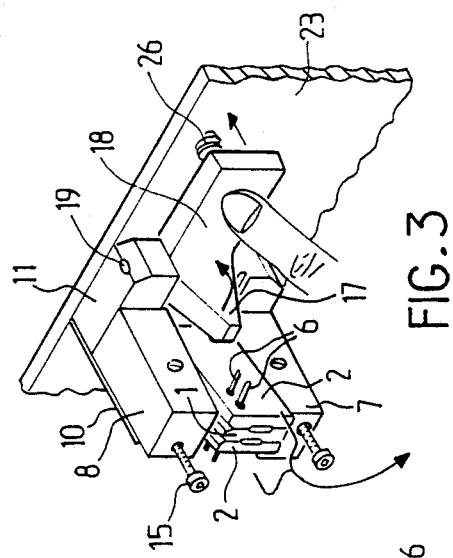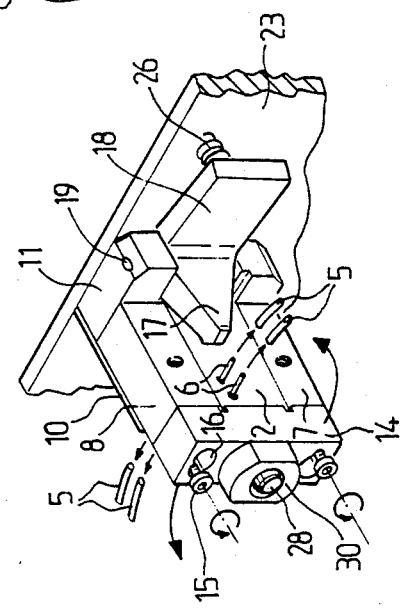

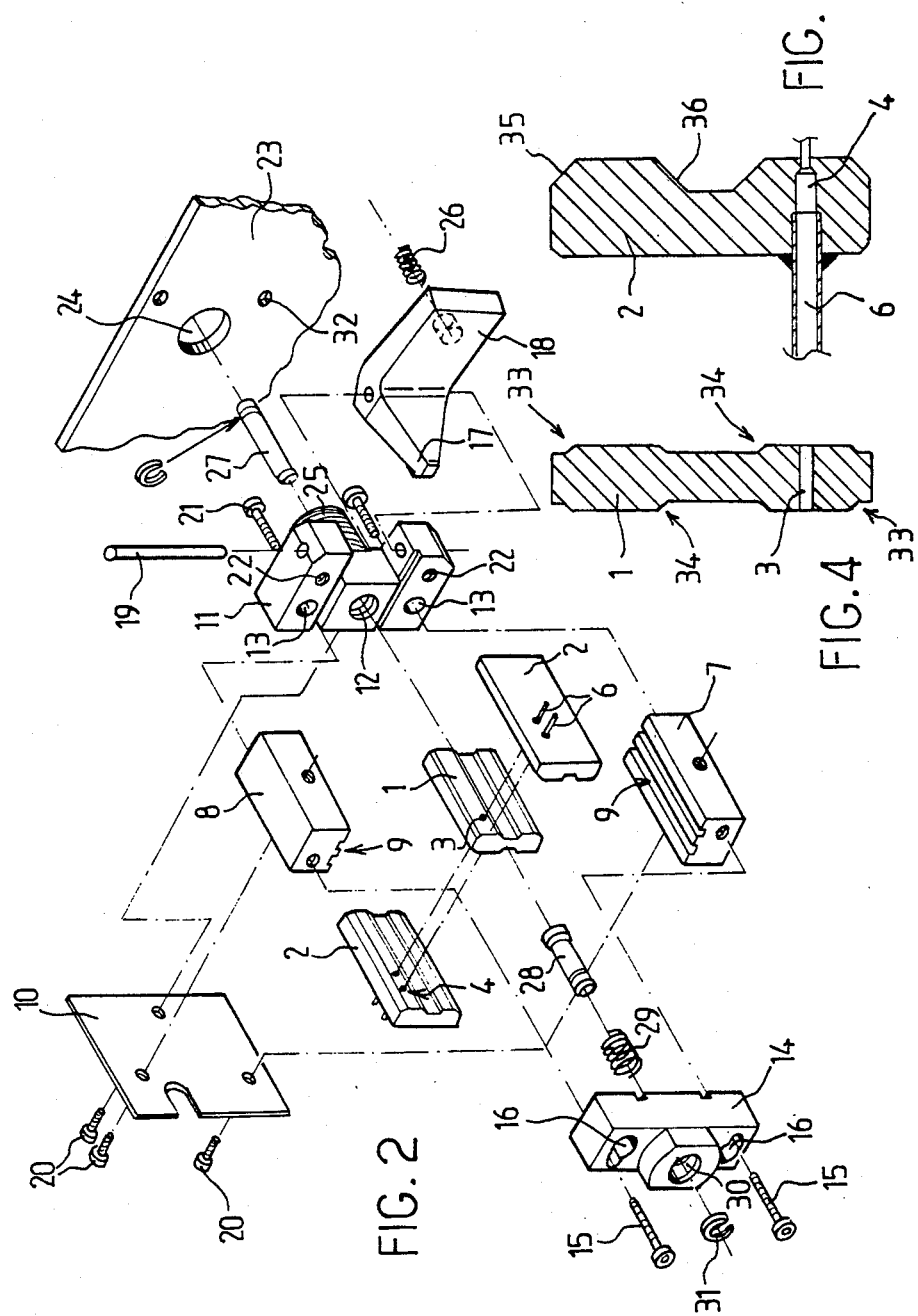

LINEAR DISPLACEMENT SAMPLING VALVE AND A DEVICE FOR FIXING SAME

BACKGROUND OF THE INVENTION

1. Field of the Invention

The invention which relates to linear displacement sampling valves, particularly for the transfer of blood samples, relates more precisely to the structure of the valve and its fixing means facilitating assembly and disassembly thereof while providing a more efficient sealing.

2. Description of the Prior Art

This type of linear displacement valve is well known, formed essentially of a central mobile element sandwiched between two fixed external elements. Said central element is provided with at least one transverse passage orifice and moves in translation from a first fixed position to a second fixed position, in each of which positions the orifice in question is aligned with one or two opposite orifices provided on the external elements for connecting two ducts together or for dividing a sample volume into segments and transferring it to another path. The central element slides between the two fixed elements under the action of an actuator rod with spring return. This type of valve lends itself particularly well to the transfer of liquids such as blood, but the ducts and the orifices must always be correctly drained and cleaned so that sampling takes place under the best conditions of operation and cleanliness. Although precise manufacturing tolerances may have been respected, and although the sealing is correct, it is always indispensable, in valves of this type, to be able to have access frequently to the main parts, namely the central mobile element and the external elements, for cleaning them, cleaning out the orifices, adjusting or improving the displacement travel of the sliding part etc..

In conventional valves, these dismantling operations are time-consuming and fastidious for they involve the unscrewing of several parts, the disconnection of the inlet and outlet ducts and the removal of protecting members, before being able to release the central parts.

Thus, for simplifying these assembly-disassembly operations at the same time as reducing the parts forming the valve, and so as to obtain an assembly of reduced size and to improve the operation thereof, the invention provides a valve and a device for fixing its elements which then avoids the drawbacks experienced with linear displacement valves of known type.

SUMMARY OF THE INVENTION

An object of the present invention consists then in providing a linear displacement sampling valve and the device for fixing its elements formed essentially by a central mobile element with at least one transverse passage orifice and adapted for effecting a sliding movement under the action of a drive means of the cylinder and piston kind, so that the transverse orifice is aligned with one or the other of several opposite orifices provided on fixed guide parts placed on each side of said central element, in which device the central sliding element and its two fixed lateral guide parts are profiled and chamfered so as to have bearing faces with a reduced friction area and form a substantially parallelepipedic assembly which is held in position on four of its faces by fixed members forming a cradle, and which is held in position on its fifth face by a manual release locking flange and on its sixth face by a clamping member of the quick release pivoting type.

More precisely, in accordance with the invention, the assembly formed by the central sliding element and the two fixed lateral guide parts bears along its lower and upper longitudinal faces on a lower guide and an upper guide secured to the same support, and along one of its end faces on a base fixed to a support plate.

According to yet other characteristics of the invention, the locking flange is fixed on the upper and lower guides and is held applied thereagainst by screws fixed to the guides, cooperating with apertures in the flange adapted for locking and unlocking said flange on the guides in the manner of a bayonet system known per se.

Furthermore, the clamping member is a rocker mounted for pivoting about a shaft fixed to the base, one end of which forms a head bearing on one of the fixed guide parts of the central assembly, a clamping spring providing the thrust of the head on the external face of said guide part.

BRIEF DESCRIPTION OF THE DRAWINGS

The following description will make clear the advantages of the invention and other special characteristics. It refers, by way of non limitative example, to the accompanying drawings which show:

FIG. 1, an general perspective view of the device for fixing the sampling valve;

FIG. 2, an exploded perspective view of the component elements of the valve and of the fixing parts;

FIG. 3, a general perspective view of the partially dismantled valve;

FIG. 4, an enlarged sectional view of the central element; and

FIG. 5 an enlarged sectional view of a fixed guide part.

DESCRIPTION OF THE PREFERRED EMBODIMENT

The sampling valve shown in the Figures uses a linear displacement central element 1 which slides with an easy fit between two fixed guide parts 2, placed on each side, the central element having a transverse passage orifice 3 adapted for being positioned, depending on the position of said element, opposite one or other of two adjacent orifices 4 provided on each lateral guide 2 and thus placing them in communication. Small flexible plastic ducts 5 are fitted on to end pieces 6 provided in line with orifices 4.

The central mobile element 1 is in the form of a rectangular plate whose four longitudinal edges 33 are chamfered and whose two largest dimension faces are formed in the middle with a longitudinal recess 34, as can be seen in FIG. 4.

Each of the two fixed lateral guide parts 2 is in the form of a rectangular plate whose longitudinal edges 35 on their face oriented towards the central mobile element 1 are chamfered and whose corresponding face is formed in the middle with a longitudinal recess 36, as shown in FIG. 5.

Thus chamfered and provided with longitudinal recesses, the central element 1 and the guide parts 2 which grip round it have bearing faces with a reduced friction area which facilitates the sealed movement of the central element with respect to the other two. Furthermore, a lower guide 7 and an upper guide 8 in the form of parallelepipedic blocks bear below and above said assembly, i.e. along its lower and upper longitudinal faces. Grooves 9 are provided on their bearing faces which reduces the friction area with the central sliding element 1. These guides 7 and 8 are fixed by one of their sides to the same vertical support plate 10 by screws 20. This plate 10 is also fixed by a screw 20 to a support base 11 on which the end face of the central element comes to bear, which base has a central opening 12 and two orifices 13 at the top and the bottom by means of which said base is also fixed by screws 21 to the lower and upper guides 7 and 8. Other orifices 22 at the top and bottom of base 11 are provided for fixing it to a support plate 23, which is a fixed plate fixed to the apparatus, or which forms part of the frame of the apparatus. This plate is formed with an opening 24 for passing a threaded sleeve 25 therethrough, provide on the rear face of the base coaxially with opening 12. Sleeve 25 serves as support for a control cylinder, not shown, placed behind plate 23. Two other orifices 32 are also provided on plate 23 for passing screws 21 therethrough for fixing base 11. Plate 10 also forms a bearing face for one of the guide parts of the central element.

On the side opposite base 11, a locking flange 14 is fixed to the lower and upper guides 7 and 8 and is held applied thereagainst by fixing screws 15 fixed in the guides and cooperating with apertures 16 in the flange, in the manner of a bayonet system so that the flange can be released by pivoting as shown by the arrows in FIG. 1.

The three central parts 1 and 2 which form a substantially parallelepipedic assembly are thus held tight in a cradle formed, on one of its longitudinal ends, by base 11, on its lower and upper edges by guides 7 and 8 and on one side by plate 10. On the side opposite this plate, on the guide part 2 there comes to bear the head 17 of a rocker 18 mounted for pivoting about a vertical shaft 19, which shaft is journalled in the support base 11 so that the rocker is hinged to this base. Rocker 18 is recalled by a clamping spring 26 bearing on plate 23, which exerts a thrust on the corresponding leg of the rocker and consequently a thrust of head 17 on the external face of the guide part 2, substantially centrally. The rocker thus forms the system for clamping three main elements of the valve.

Finally, the central sliding element 1 driven between the guide parts 2 by the rod of the piston and cylinder not shown, and through a control shaft 27 which passes through sleeve 25 and opening 12 to come into abutment against the end of the central element 1. On the other side thereof, a return shaft 28 comes into abutment on which is fitted a spring 29 whose end is immobilized in a central orifice 30 of flange 14 by a clip 31. The central elements 1 and 2 of the sampling valve are thus held on all sides as shown in FIG. 1. When it is desired to dismantle the valve, the small ducts 5 are first of all released directly from end pieces 6 on which they are fitted and screws 15 are unscrewed a few turns as shown by the arrows. Then the locking flange 14 is gripped and, by rotating it in the direction of the arrows in FIG. 1, the largest diameter portions of each aperture 16 are released from the head of each screw 15 so that said flange may then be released forwards. By releasing the flange, the spring 29 and the return shaft 28 are also released, which, because of their configuration, remain held in the orifice 30 of said flange. Finally, a pressure is exerted on the rocking lever 18, as shown in FIG. 3. This action causes the rocker 18 to pivot about its shaft 19 against the force of the clamping spring 26, and the head 17 of the rocker consequently moves away from the external wall of the fixed guide part 2. The assembly formed by the three central elements 1 and 2 may then be rapidly released forwards, as shown by the arrow in Figure 3. Since these parts bear on one another they can be readily separated and inspected and cleaned without difficulty. For refitting, pressure is again applied on the rocking lever 18 so as to be able to replace them in the correct position between the lower and upper guides 7 and 8, before refitting the locking flange 14 and connecting the small ducts 5.

Sealing of the valve during operation is efficient because the force of the adjustment spring 26 is exerted through the head 17 of the rocker, in the center of the valve, which thus distributes the application pressure. Furthermore, because of the special profile of the central element and of the guide parts which surround it, the friction areas are reduced and the displacement of the central element 1 is easy with a low power cylinder. Moreover, because of the reduced number of parts used, said valve is of a low cost. Finally, as can be seen in FIG. 1, the members which surround and hold the central element in position are of restricted dimensions; thus, the sampling valve is of a reduced size which makes it possible to position it as close as possible to the sample taking means and thus reduce the connection lengths.

What is claimed is:

1. In a linear displacement sampling valve and a device for fixing the elements thereof formed essentially by a central mobile element with at least one transverse passage orifice and adapted for effecting a sliding movement under the action of a drive means of the cylinder and piston kind, so that the transverse orifice is aligned with one or the other of several opposite orifices provided on fixed guide parts placed on each side of said central element, said central sliding element and its two fixed lateral guide parts are profiled and chamfered so as to have bearing faces with a reduced friction area and form a substantially parallelepipedic assembly which is held in position on four of its faces by fixed members forming a cradle therefor, and which is held in position on a fifth face thereof by a manual release locking flange and on its sixth face by a clamping member of the quick release pivoting type.

2. The sampling valve as claimed in claim 1, wherein said central mobile element is in the form of a rectangular plate whose four longitudinal edges are chamfered and having two large dimensional faces which each have a longitudinal recess in the middle thereof.

3. The sampling valve as claimed in claim 1, wherein said lateral guide parts are each in the form of a rectangular plate in which the longitudinal edges of the face oriented towards the central mobile element are chamfered and whose corresponding face has in the middle a longitudinal recess.

4. The sampling valve as claimed in claim 1, wherein end pieces are provided on the external face of each fixed lateral guide part (2), in line with said transverse passage orifices.

5. The sampling valve as claimed in claim 1, wherein the assembly formed by said central sliding element and said two fixed lateral guide parts bears along its lower and upper longitudinal faces on a lower guide and an upper guide secured to the same fixed support.

6. The sampling valve as claimed in claim 5 wherein said fixed support to which said lower and upper guides are attached is a holding plate forming a lateral face of the cradle for the central assembly and said holding plate is itself fixed to the support base.

7. The sampling valve as claimed in claim 5, wherein said guides are provided wth longitudinal grooves on their face bearing on the central assembly.

8. The sampling valve as claimed in claim 1, wherein the assembly formed by said central sliding element and said two fixed lateral guide parts bears along one of its end faces on a base fixed to a support plate.

9. The sampling valve as claimed in claim 8, characterized in that said plate is formed with an opening for passing a threaded sleeve therethrough, projecting from the rear face of the base and coaxial with an opening provided at the centre of said base.

10. The sampling valve as claimed in claim 1, wherein said locking flange is fixed to the lower and upper guides and is held applied theragainst by screws fixed in the guides, cooperating with apertures in the said flange for locking or unlocking said flange on the guides in the manner of a bayonet system, known per se.

11. The sampling valve as claimed in claim 1, wherein said clamping member is a rocker mounted for pivoting about a shaft fixed to the base, one end of which forms a head bearing on one of the fixed guide parts of the central assembly, a clamping spring providing the thrust of the head on the external face of said fixed guide part.

12. The sampling valve as claimed in claim 1, wherein said central mobile element is operated on one side by means of a control shaft, passing through the sleeve and the base, a return shaft coming into abutment on the other side of said mobile element and cooperating with a spring held in position by the locking flange.

* * * * *